United States Patent
Naiki et al.

(10) Patent No.: US 6,251,929 B1
(45) Date of Patent: Jun. 26, 2001

(54) THERAPEUTIC AGENT FOR INTRACTABLE VASCULITIS

(75) Inventors: Mitsuru Naiki; Takumi Numazawa; Tomoyuki Okada; Kazuharu Ienaga; Kazuyoshi Sawada, all of Katoh-gun (JP)

(73) Assignee: Nippon Zoki Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 09/434,494

(22) Filed: Nov. 5, 1999

(30) Foreign Application Priority Data

Nov. 16, 1998 (JP) ................................. 10-324790

(51) Int. Cl.⁷ .................................. A64K 31/415
(52) U.S. Cl. ........................................... 514/390
(58) Field of Search ............................. 514/390

(56) References Cited

U.S. PATENT DOCUMENTS

| | | |
|---|---|---|
| Re. 32,919 | 5/1989 | Sarnoff . |
| 3,818,031 | 6/1974 | Baerlocher et al. . |
| 4,096,130 | 6/1978 | Kraft et al. . |
| 4,281,009 | 7/1981 | Konishi . |
| 4,647,574 | 3/1987 | Ienaga et al. . |

(List continued on next page.)

FOREIGN PATENT DOCUMENTS

| | | |
|---|---|---|
| 563 711 | 7/1975 | (CH) . |
| 2 214 448 | 10/1972 | (DE) . |
| 26 12 926 A1 | 10/1977 | (DE) . |
| 0 780 125 | 6/1977 | (EP) . |
| 0 160 618 | 11/1985 | (EP) . |
| 0 194 226 | 9/1986 | (EP) . |
| 0 353 198 A1 | 1/1990 | (EP) . |
| 0 412 940 A2 | 2/1991 | (EP) . |
| 0 718 289 A1 | 6/1996 | (EP) . |
| 0 718 290 A1 | 6/1996 | (EP) . |
| 0721 944 | 7/1996 | (EP) . |
| 61/122275 | 6/1986 | (JP) . |
| 62/14 | 1/1987 | (JP) . |
| 63-166870 | 7/1988 | (JP) . |
| 64-56614 | 3/1989 | (JP) . |
| 2019363 | 1/1990 | (JP) . |
| 2-40368 | 2/1990 | (JP) . |
| 2-167264 | 6/1990 | (JP) . |
| 2225485 | 9/1990 | (JP) . |
| 3-204874 | 9/1991 | (JP) . |
| 6-135968 | 5/1994 | (JP) . |
| 6-67827 | 8/1994 | (JP) . |
| 6-305964 | 11/1994 | (JP) . |
| 7-133264 | 5/1995 | (JP) . |
| 8-157473 | 6/1996 | (JP) . |
| WO 85 05103 | 11/1985 | (WO) . |
| WO 86/01110 | 2/1986 | (WO) . |
| WO 89/02890 | 4/1989 | (WO) . |

OTHER PUBLICATIONS

European Search Report for EP 97122861, published May 15, 1998.
Malamas, "Quinazolineacetic Acid and Related Analogues as Aldose Reductase Inhibitors" *J. Med. Chem.* (1991), 34, (4), 1492–503.
Patton, *J. Org. Chem*, 32, No. 2, pp. 383–388 (1967).
Brownlee et al., "Aminoguanidine Prevents Diabetes–Induced Arterial Wall Protein Cross–Linking", *Science*, vol. 232, 1986, pp. 1629–32.
Ishii, et al., "Highly Selective Aldose Reductase Inhibitors", *J. Med Chem.*, vol. 39, No. 9, 1996, pp. 1924–1927.
Kato, et al., "Polyol Metabolism and Glycation in Diabetic Neuropathy", *Diabetes Front*, vol. 8, No. 4, 1997, pp. 510–511.
Kotani et al., "Highly Selective Aldose Reductase Inhibitors. 3." *J. Med Che,.*, vol. 40, No. 5, 1997, pp. 684–694.
Kotani et al., "Highly Selective Aldose Reductase Inhibitors. II", *Chem. Pharm. Bull.*, vol. 45, No. 2, 1997, pp. 297–304.
K. Ogawva, et al., "Syntheses of substituted 2,4–dioxo–thienopyrimidin–1–acetic acids and their evaluation as aldose reductase inhibitors", *European Journal of Medicinal Chemistrychimica Therapeutica*, vol. 28, No. 10, 1993, pp. 769–781.
Morrison and Boyd, *Organic Chemistry*, Allyn and Bacon, Inc., Boston (1965), pp. 806, 808, 847–848.

(List continued on next page.)

Primary Examiner—Theodore J. Criares
(74) Attorney, Agent, or Firm—Hollander Law Firm, P.L.C.

(57) ABSTRACT

A highly safe therapeutic agent for intractable vasculitis such as malignant rheumatoid arthritis contains a hydantoin derivative represented by the formula (I) or a pharmaceutically acceptable salt thereof as an effective ingredient:

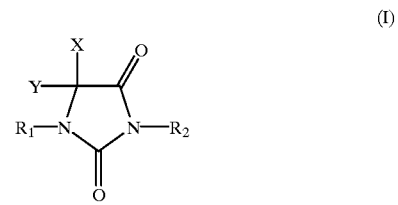

wherein each of $R_1$, and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group. The hydantoin derivatives significantly suppress the generation of arthritis and arteritis (cutaneous ulcer and auricular infarcted necrosis) which are naturally developed in model animals (MRL/lpr), and further significantly elongate the survival rate of MRL/lpr mice. Consequently, the hydantoin derivatives, having low toxicity and little side effects are very useful as highly safe therapeutic agents for intractable vasculitis such as malignant rheumatoid arthritis.

20 Claims, 4 Drawing Sheets

U.S. PATENT DOCUMENTS

| | | |
|---|---|---|
| 4,656,034 | 4/1987 | Sarnoff. |
| 4,658,830 | 4/1987 | Sarnoff. |
| 4,661,469 | 4/1987 | Sarnoff. |
| 4,683,240 | 7/1987 | Ienaga et al.. |
| 4,772,585 | 9/1988 | Sarnoff et al.. |
| 4,832,682 | 5/1989 | Sarnoff. |
| 4,985,453 | 1/1991 | Ishii et al.. |
| 5,002,930 | 3/1991 | Sarnoff et al.. |
| 5,078,680 | 1/1992 | Sarnoff. |
| 5,084,473 | 1/1992 | Mikami et al.. |
| 5,340,829 | 8/1994 | Clark et al.. |
| 5,681,843 | 10/1997 | Kotani et al.. |
| 5,912,261 | 6/1999 | Kotani et al.. |
| 6,040,326 | 3/2000 | Hotta et al.. |

OTHER PUBLICATIONS

White, R. H. et al., "Hypertension, Hyperreninemia, and Secondary Hyperaldosteronism in Systemic Necrotizing Vasculitis" *Annuals of Internal Medicine*, US, New York, NY, vol. 92, No. 2, Part 1, Feb. 1980, pp. 199–201, XP000856338.

Kirsch, "Evidence for Free Radical Mechanisms of Brain Injury Resulting from Ischemia/Reperfusion–Induced Events," *Journal of Neurotrauma*, vol. 9, Supplement 1, 1992, pp. S157–S163.

Greenwald, "Therapeutic Usages Of Oxygen Radical Scavengers in Human Diseases: Myths and Realities," *Free Rad. Res. Comms.*, vol. 12–13, pp. 531–538, 1991.

Greenwald, "Superoxide Dismutase and Catalase As Therapeutic Agents For Human Diseases," *Free Radical Biology & Medicine*, vol. 8, pp. 201–209, 1990.

Rice–Evans et al., "Current Status Of Antioxidant Therapy," *Free Radical Biology & Medicine*, vol. 15, pp. 77–96, 1993.

Kanazu et al., "Aldehyde reductase is a major protein associated with 3–deoxyglucosone reductase activity in rat, pig and human livers," *Biochem J.*, 279, 903–906 (1991).

Flynn, "Aldehyde Reductases: Monomeric Nadph–Dependent Oxidoreductases With Multifunctional Potential," *Biochem. Pharmacol.*, vol. 31, No. 17, 2705–2712 (1982).

"Pathologic Biochemistry and Clinics of Free Radicals, Inflammation and Antiinflammation," *Nippon Rinsho*, vol. 46, No. 10, pp. 93–97 (1988).

Yonezawa et al., *Nippon Kagaku Zasshi*, 89, No. 8, pp. 62–64 (1968).

Miyanoshita et al., "Inhibitory Effect Of Cyclic AMP On Phorbol Ester–Stimulated Production of Reactive Oxygen Metabolites in Rat Glomeruli," *Biochemical and Biphysical Research Communication*, vol. 165, No. 1, 1989, pp. 519–525.

Grangier et al., "Reactivity of Nucleophilic Uracil Derivatives," *J. Heterocyclic Chem.* (1994), 31 (6), 1707–14.

Krasnov et al. (CA 119:8771, abstract of *Zh. Org. Khim.* (1992), 28(7), 1531–7.

Ishii et al. (CA 119:180804, abstract of JP 05043555) 1993.

Henmi et al. (CA 113:23919, abstract of JP 02019363) 1990.

Average

After deviation was checked by a Kruskal-Wallis test, the significant difference to the control group by means of a multiple comparison (Dunnet method).

Fisher's direct probability method
** ; p<0.01

THERAPEUTIC AGENT FOR INTRACTABLE VASCULITIS

FIELD OF THE INVENTION

The present invention relates to a therapeutic agent for intractable vasculitis containing a hydantoin derivative or a pharmaceutically acceptable salt thereof as an effective ingredient.

BACKGROUND OF THE INVENTION

The term "intractable vasculitis" is a specific classification term in Japan and it stands for a group of vasculitis syndrome belonging to intractable diseases. According to the "Gist of Measures for Intractable Diseases" issued by the Japanese Government, an intractable disease is defined as: 1) a disease where the cause is ambiguous, the therapeutic method therefor has not been established and there is great risk of sequela, and 2) a disease where the progress is rather chronic and, since it involves both an economic burden and significant labor for nursing etc., home-care is burdensome and mental health is strained. Specific examples of intractable vasculitis, which is one of the syndromes of intractable diseases, defined as such are: periarteritis nodosa (PN), Wegener's granulomatosis (WG), malignant rheumatoid arthritis (MRA), Kawasaki disease vasculitis, Takayasu's arteritis, Buerger's disease, blood vessel Behcet disease, vasculitis of collagen disease, allergic granulomatous vasculitis, nonspecific inflammatory abdominal aortic aneurysm (IAAA), vasculitis related to anti-neutrophil cell antibody (ACNA), anti-phospholipid antibody syndrome and hypersensitive vasculitis. The concept and classification of those intractable diseases are mentioned in detail in a review by Professor Nagasawa (Rinsho Kagaku, 33(11), 1383–1387), etc.

Malignant rheumatoid arthritis (MRA), which is one of the intractable vasculitis diseases, is defined as a disease accompanied by intractable or severe clinical symptoms showing extra-articular symptoms such as vasculitis in addition to the symptoms of chronic rheumatoid arthritis (RA). It had been known that there is a case where RA is accompanied by vasculitis. Then, in 1954, Bevans et al reported two RA cases complicated with nodular polyarteritis-like vasculitis resulting in quick death and they proposed to call such a case "MRA" in view of its bad prognosis. This is the reason for the naming of MRA. In RA, various immune abnormalities such as the presence of rheumatoid factors (RF) in blood are present. However, in MRA, much more and significant abnormalities than common RA are noted, such as an increase of immune complex in blood, lowering of serum complement, and a positive anti-nuclear antibody. Unlike RA where no death occurs, MRA has a characteristic feature that there are many fatal cases due to extra-articular symptoms such as infectious diseases, vasculitis, rheumatoid lung and amyloidosis.

The number of patients suffering from MRA in Japan is estimated to be from 2,000 to 3,000 (about 0.6% of the patients suffering from RA). The age of onset of MRA has a peak in the fifties and that is a bit higher age than in the case of RA. With regard to sexuality, the proportion of male patients is more than the case of RA, and the ratio of patients in terms of male:female is about 1:2. Although MRA shares features with RA, it is characteristic that its extra-articular symptom is more significant than common RA, that the percentage of death thereby is high and that there is an immune abnormality in its base. Accordingly, in the therapy of MRA, it is necessary to take the therapy for an extra-articular symptom into consideration in addition to the therapy for common RA and it is particularly necessary to place more importance on the therapy for immune abnormality.

As an anti-inflammatory therapy, nonsteroidal anti-inflammatory drugs (NSAIDs) and steroidal anti-inflammatory drugs are used for the therapy of RA. Although NSAIDs are the basic therapeutic agents for articular diseases, their efficacy to extra-articular diseases is not so clear. In addition, MRA has a tendency that articular symptoms are ameliorated during the period where the extra-articular symptoms are significant. Thus, it is difficult to evaluate the usefulness of the NSAIDs in the therapy of MRA and that has not been clarified yet. On the other hand, steroids are used as basic therapeutic agents for RA. However, since the onset of MRA often happens due to a sudden increase or decrease of steroids, it has been said that their use must be careful. It has been reported that a steroid pulse therapy where intravenous drip infusion of 1,000 mg of methylpredonisolone is carried out for three days is useful for severe refractory RA and is useful not only for improvement in clinical symptoms but also for suppression of immune complex in blood and RF. However, when the pulse therapy is finished, there is a tendency that the state returns to the previous one within a relatively short period. Therefore, to maintain the effect, it is necessary to also conduct immunotherapy together with the pulse therapy. Although it is likely that the pulse therapy is effective for MRA symptoms, the effect is not long-lasting and the said therapy is not able to be repeated frequently. Accordingly, pulse therapy is considered to be an emergency therapy at present.

With regard to the drugs for immunotherapy, immunomodulators and immunosuppressants are used. Slowly-acting anti-rheumatic agents such as gold sodium thiomalate (GST) and d-penicillamine (d-p) are classified as immunomodulators because of a sense that they improve the immune abnormality of RA but do not suppress the normal immune mechanism. It is believed that GST mainly functions via the macrophage mechanism while d-p improves RA by means of suppression of T-helper cell function. However, immunomodulators are slow-acting and do not serve the purpose when used after an MRA symptom occurs. In addition, their efficacy towards severe MRA symptoms has not been confirmed yet.

Although steroids and NSAIDs have an immunosuppressing action, the term "immunosuppressant" usually means cytotoxic drugs such as cyclophosphamide (CY), azathioprine (AZ), methotrexate (MTX), etc. and cyclosporin A (CsA). CY is an alkylating agent and damages DNA by inhibiting its synthesis whereby it achieves an immunosuppressing action. Although this agent has been proved to be effective towards RA by a double blind test, its allowed use is limited to severe RA where common therapy is not effective due to its strong side effect. It has also been reported that they are effective towards vasculitis. AZ and MTX are antimetabolic immunosuppressants and it has been reported that, although they have weaker side effects than CY, their immunosuppressing action is weak as well. Effect of the MTX therapy to MRA is ambiguous and it is believed that its intermittent administration in low doses will probably have a therapeutic significance only as an immunomodulator. The action mechanism of CsA is believed to be mostly due to suppression against IL-2 production of the T-helper cell function and due to inhibition against IL-2 receptor expression of cytotoxic cells. With regard to the efficacy of CsA towards RA, Dougados et al reported that, in a double blind test, it showed a significant improving effect compared to the control group but it resulted in nephropathy in about one half of the treated group.

As mentioned above, the drugs used for the therapy of intractable vasculitis such as malignant rheumatoid arthritis at present have their merits and demerits in view of expression of pharmaceutical effects and onset of side effects. Thus, no suitable therapeutic agent has yet been found and there is a strong demand in the clinical field for therapeutic agents having high safety and strong therapeutic effect.

Several compounds of the present invention were found as novel substances having growth suppressing action to plants. As a result of subsequent investigations, those compounds including analogs thereof have been found to have pharmacological actions such as hypoglycemic action and hypolipemic action and to exhibit low toxicity resulting in almost no side effects. See U.S. Pat. Nos. 4,647,574 and 4,683,240, each to Ienaga et al and Japanese Laid-Open Patent Publications Sho-57/114578, Sho-60/188373, Sho-61/122275, Sho-62/45525, Sho-62/14, Hei-01/75473, Hei-01/299276, etc.). It has been also reported that the compounds of the present invention are useful as agents for lowering uremic toxin (Japanese Laid-Open Patent Publication Hei-03/72463) and further that they are useful as eliminators of active oxygen and free radicals (Japanese Laid-Open Patent Publication Hei-09/227377). However, none of the above-mentioned patent publications, describe a therapeutic effect of the compounds of the present invention for intractable diseases such as malignant rheumatoid arthritis and, in addition, there has been no report suggesting that at all.

The present inventors have carried out intensive investigations and have found that the hydantoin derivatives of the present invention have a therapeutic effect for malignant rheumatoid arthritis whereupon the present invention has been accomplished. The compounds of the present invention are less toxic and have almost no side effect, and accordingly they are quite useful as safe drugs for the therapy of intractable vasculitis such as malignant rheumatoid arthritis.

The present invention solves the above-mentioned problems and provides a highly safe therapeutic agent for intractable diseases such as malignant rheumatoid arthritis which has been strongly demanded by patients and the clinical field.

SUMMARY OF THE INVENTION

The hydantoin derivatives and their pharmaceutically acceptable salts of the present invention may be used as therapeutic and preventive agents for intractable vasculitis such as malignant rheumatoid arthritis (MRA), periarteritis nodosa (PN), Wegener's granulomatosis (WG), Kawasaki disease vasculitis, Takayasu's arteritis, Buerger disease, blood vessel Behcet disease, vasculitis of collagen disease, allergic granulomatous vasculitis, nonspecific inflammatory abdominal aortic aneurysm (IAAA), vasculitis related to anti-neutrophil cell antibody (ACNA), anti-phospholipid antibody syndrome and hypersensitive vasculitis.

The pharmaceutical compositions employed in the present invention include at least one hydantoin derivative represented by the general formula (I) or pharmaceutically acceptable salts of the derivatives represented by the general formula (I):

(I)

wherein each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together represent an oxo group.

The hydantoin derivatives may be administered orally or parenterally to patients in need of treatment in pharmaceutically effective amounts with little, if any side effects, low toxicity, and high safety.

DETAILED DESCRIPTION OF THE INVENTION

The effective ingredient of the therapeutic agent for intractable vasculitis according to the present invention is a hydantoin derivative represented by the following formula (I) or a pharmaceutically acceptable salt thereof:

(I)

wherein each of $R_1$ and $R_2$, which may be the same or different, represents hydrogen, an alkyl group or a cycloalkyl group; and each of X and Y, which may be the same or different, represents hydrogen, a hydroxyl group, an alkyl group or an alkoxy group, or X and Y together represent an oxo group.

In the above mentioned formula (I), each of $R_1$, and $R_2$, which may be the same or different, represents hydrogen, an alkyl group, preferably a straight or branched alkyl group having 1 to 20 carbon atoms such as methyl, ethyl, propyl, isopropyl, butyl, isobutyl, sec-butyl, t-butyl, pentyl, isopentyl, neopentyl, t-pentyl, hexyl, dimethylbutyl, heptyl, octyl, nonyl, decyl or stearyl; or a cycloalkyl group, preferably a cycloalkyl group having 3 to 8 carbon atoms such as cyclopropyl, cyclobutyl, cyclopentyl, cyclohexyl, cycloheptyl or cyclooctyl.

Each of X and Y, which may be the same or different, represents hydrogen, a hydroxyl group, an alkyl group, preferably a straight or branched alkyl group having 1 to 3 carbon atoms such as methyl, ethyl, propyl, isopropyl; or an alkoxy group, preferably a straight or branched alkoxy group having 1 to 5 carbon atoms such as methoxy, ethoxy, propoxy, isopropoxy, butoxy, isobutoxy, sec-butoxy, t-butoxy, pentoxy, isopentoxy, neopentoxy; or X and Y together represent an oxo group.

Preferred compounds of the present invention are:
[Compound 1] Hydantoin
[Compound 2] 1-Methylhydantoin
[Compound 3] 3-Methylhydantoin
[Compound 4] 1-Ethylhydantoin
[Compound 5] 1-Propylhydantoin
[Compound 6] 1-Butylhydantoin
[Compound 7] 1-t-Butylhydantoin
[Compound 8] 1-Hexylhydantoin
[Compound 9] 1-(1,3-Dimethylbutyl)hydantoin
[Compound 10] 1-Decylhydantoin
[Compound 11] 1-Stearylhydantoin
[Compound 12] 1,3-Dimethylhydantoin
[Compound 13] 1,5-Dimethylhydantoin
[Compound 14] 3,5-Dimethylhydantoin
[Compound 15] 1-Cyclopentylhydantoin
[Compound 16] 1-Cyclohexylhydantoin
[Compound 17] 1-Cyclohexyl-3-methylhydantoin
[Compound 18] 3-Cyclohexylhydantoin
[Compound 19] 1,3-Dicyclohexylhydantoin
[Compound 20] 5-Hydroxyhydantoin
[Compound 21] 5-Hydroxy-1-methyihydantoin
[Compound 22] 5-Hydroxy-3-methylhydantoin
[Compound 23] 5-Hydroxy-1-ethylhydantoin
[Compound 24] 5-Hydroxy-1-propylhydantoin
[Compound 25] 5-Hydroxy-1-butylhydantoin
[Compound 26] 5-Hydroxy-1-t-butylhydantoin
[Compound 27] 5-Hydroxy-1-hexylhydantoin
[Compound 28] 5-Hydroxy-1-(1,3-dimethylbutyl)hydantoin
[Compound 29] 5-Hydroxy-1-decylhydantoin
[Compound 30] 5-Hydroxy-1-stearylhydantoin
[Compound 31] 5-Hydroxy-1-cyclopentylhydantoin
[Compound 32] 5-Hydroxy-1-cyclohexylhydantoin
[Compound 33] 5-Hydroxy-1-cyclohexyl-3-methylhydantoin
[Compound 34] 5-Hydroxy-1,3-dimethylhydantoin
[Compound 35] 5-Hydroxy-1,5-dimethylhydantoin
[Compound 36] 5-Hydroxy-3,5-dimethylhydantoin
[Compound 37] 5-Hydroxy-1,3-dicyclohexylhydantoin
[Compound 38] 5-Methoxyhydantoin
[Compound 39] 5-Methoxy-1-methylhydantoin
[Compound 40] 5-Methoxy-3-methylhydantoin
[Compound 41] 5-Methoxy-1-ethylhydantoin
[Compound 42] 5-Methoxy-1-propylhydantoin
[Compound 43] 5-Methoxy-1-butylhydantoin
[Compound 44] 5-Methoxy-1-cyclohexylhydantoin
[Compound 45] 5-Methoxy-3-cyclohexylhydantoin
[Compound 46] 5-Ethoxyhydantoin
[Compound 47] 5-Ethoxy-1-methylhydantoin
[Compound 48] 5-Ethoxy-3-methylhydantoin
[Compound 49] 5-Ethoxy-1-ethylhydantoin
[Compound 50] 5-Ethoxy-1-propylhydantoin
[Compound 51] 5-Ethoxy-1-butylhydantoin
[Compound 52] 5-Propoxyhydantoin
[Compound 53] 5-Propoxy-1-methylhydantoin
[Compound 54] 5-Propoxy-3-methylhydantoin
[Compound 55] 5-Propoxy-1-ethylhydantoin
[Compound 56] 5-Propoxy-1-propylhydantoin
[Compound 57] 5-Propoxy-1-butylhydantoin
[Compound 58] 5-Butoxyhydantoin
[Compound 59] 5-Butoxy-1-methylhydantoin
[Compound 60] 5-Butoxy-3-methylhydantoin
[Compound 61] 5-t-Butoxyhydantoin
[Compound 62] 5-t-Butoxy-1-methylhydantoin
[Compound 63] 5-t-Butoxy-3-butylhydantoin
[Compound 64] Imidazolidinetrione
[Compound 65] 1-Methylimidazolidinetrione
[Compound 66] 1-Ethylimidazolidinetrione
[Compound 67] 1-Butylimidazolidinetrione
[Compound 68] 1-Isobutylimidazolidinetrione
[Compound 69] 1-t-Butylimidazolidinetrione
[Compound 70 ] 1-Hexylimidazolidinetrione
[Compound 71] 1-(1,3-Dimethylbutyl)imidazolidinetrione
[Compound 72] 1-Decylimidazolidinetrione
[Compound 73] 1-Cyclopentylimidazolidinetrione
[Compound 74] 1-Cyclopentyl-3-ethylimidazolidinetrione
[Compound 75] 1-Cyclohexylimidazolidinetrione
[Compound 76] 1,3-Dimethylimidazolidinetrione
[Compound 77] 1,3-Dicyclohexylimidazolidinetrione The hydantoin derivatives of the present invention include the pharmaceutically acceptable salts of the compounds represented by the above given formula (I). Exemplary salts of the present invention are acid addition salts of the hydantoin derivatives of general formula (I) with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid, or sulfanilic acid. Other salts of the present invention include salts of the hydantoin derivatives of general formula (I) with: a) an alkali metal such as sodium and potassium, b) an alkaline-earth metal such as calcium, magnesium and barium, and c) other metals such as aluminum and zinc.

The pharmaceutically acceptable salts may be manufactured by conventional methods, starting from the hydantoin derivatives of the present invention in a free state or free form, or by conversion from one salt to another salt.

When there are steric isomers or stereoisomers such as cis-trans isomers, optical isomers, or conformational isomers, hydrates or complexes for the compounds of the present invention, the present invention includes any and all of such isomers, hydrates and complexes.

The compounds of the present invention may be manufactured by conventional methods as disclosed, for example, in Japanese Laid Open (Kokai) Nos. 61/122275 (published Jun. 10, 1986) and 62/14 (published Jan. 6, 1987) and their corresponding U.S. Pat. Nos. 4,647,574 and 4,683,240 each to Ienaga et al, respectively. The disclosures of each of said Japanese publications and U.S. Pat. Nos. 4,647,574 and 4,683,240 are herein incorporated by reference in their entireties. For example, hydantoin derivatives of the present invention may be produced by methods as disclosed in U.S. Pat. No. 4,647,574 at column 2 line 39 to column 3 line 32. Thus, the hydantoin derivatives may be produced by first conventionally esterifying a glyoxylic acid. For example, a glyoxylic acid is reacted with an alcohol or 2-methoxyethanol, at room temperature or at a suitable temperature above room temperature or under reflux, for about several hours to about a day, with the produced water being removed, in the presence of an organic acid catalyst such as p-toluene-sulfonic acid or camphorsulfonic acid in an aprotic solvent such as benzene, toluene, xylene or carbon tetrachloride. Then the produced glyoxylic acid ester or an o-alkylglyoxylic acid ester (glyoxylic acid ester alcoholate) is, without being isolated or further purified, reacted at room temperature or heated under reflux for about 1 hour to about several days with, e.g., N-alkylurea, N-cycloalkylurea, N,N' dialkylurea or N,N'-dicycloalkylurea in an appropriate solvent such as water, acetic acid or alcohol, such as butanol or mixtures thereof, to give compounds of the present invention represented by the general formula (I).

The above-mentioned reaction can also be carried out with an α-ketocarbonic acid such as pyruvic acid as the starting material instead of a glyoxylic acid.

The compounds of the present invention wherein X or Y is an alkoxy group may be produced from a hydantoin derivative as prepared, e.g., by the process described above, by a conventional O-alkylation process. The hydantoin derivatives may be reacted with p-toluenesulfonyl chloride or mesyl chloride to introduce a removable residue into the hydroxy group at the 5-position, in the presence of an organic base such as a lower alkylamine or an alkali metal alkoxide in an appropriate solvent which does not inhibit the reaction. During or after the reaction, the resultant product is reacted with the alcohol corresponding to the X or Y substituent of the desired hydantoin derivative to give the compound of the present invention. This O-alkylation may be carried out at room temperature or at a suitable temperature above room temperature or under reflux, for about several hours to about several days.

The compounds of the present invention also include products from the N-alkylation of the hydantoin derivatives. The hydantoin derivative is reacted with a halogenated alkyl, a halogenated cycloalkyl, a dialkylsulfuric acid such as dimethylsulfonic acid, a p-toluenesulfonic acid alkyl ester or a p-toluenesulfonic acid cycloalkyl ester, in the presence of a base such as a lower alkyl amine, an alkali metal alkoxide or a hydroxyalkyl metal in an appropriate solvent which does not inhibit the reaction such as absolute alcohol, or dimethyl sulfoxide. The N-alkylation may be carried out at room temperature or at a suitable temperature above room temperature for about several hours to about several days.

When X and Y represent an oxo group, the hydantoin derivatives or imidazolidinetrione derivatives of the present invention may be produced by methods as disclosed in T. Yonezawa et al, Nippon Kagaku Zasshi, 89, No. 8, pp 62–64 (1968), Tad L. Patton, J. Org. Chem., 32, No. 2, 383–388 (1967), and U.S. Pat. No. 4,683,240 at column 3 lines 27–49. For example, as disclosed in U.S. Pat. No. 4,683,240, oxalyl chloride and an N-substituted urea, such as an N-alkylurea, or N-cycloalkylurea may be stirred in an appropriate solvent such as tetrahydrofuran which does not inhibit the reaction in an ice-water bath or at room temperature. Alternatively, diethyl oxalate and the above-mentioned N-substituted urea may be stirred in an appropriate solvent which does not inhibit the reaction in the presence of an organic base such as an amine or alkali metal alkoxide at room temperature, if desired, by heating to higher temperatures to give the imidazolidinetrione derivatives of the present invention.

The compounds of the invention can also be prepared by conventional N-alkylation wherein unsubstituted, 1-alkylsubstituted or 1-cycloalkylsubstituted imidazolidinetrione is reacted with halogenated alkyl.

The compounds of the present invention prepared as described above may be purified by conventional methods such as distillation, chromatography and recrystallization. The compounds may be identified by means of, for example, elementary analysis, melting point measurement, infrared (IR), nuclear magnetic resonance (NMR), ultraviolet (UV), and mass spectroscopy (MS).

The compounds of the present invention, which include the hydantoin derivatives and their pharmaceutically acceptable salts and complexes, can be made into pharmaceutical preparations by combining one or more of the compounds with at least one pharmaceutically acceptable carrier or diluent. Any of the known methods for providing preparations, such as for oral administrations (e.g. tablets, capsules, powders, liquids, etc.) and for parenteral administrations (e.g. for subcutaneous, intravenous, intramuscular, intrarectal and intranasal administrations) may be used to produce the pharmaceutical compositions of the present invention. In preparing the preparations, the hydantoin derivatives of the present invention may be used in the form of their pharmaceutically acceptable salts. The compounds of the present invention may be used either solely or jointly in pharmaceutically effective amounts for treating animals or humans. The compounds of the invention can be used either solely or jointly together in pharmaceutically acceptable amounts with pharmaceutically effective amounts of other pharmaceutically active components in pharmaceutical compositions or preparations.

In the case of preparations for oral administration, one or more of the compounds of the present invention either alone or in combination with commonly-used pharmaceutically acceptable excipients in pharmaceutically acceptable amounts such as at least one suitable pharmaceutically acceptable additive or carrier (e.g. lactose, mannitol, corn starch, potato starch, potassium citrate, etc.) may be mixed with one or more pharmaceutically acceptable: (1) binders such as cellulose derivatives (e.g. crystalline cellulose, hydroxypropylcellulose, etc.), gum arabicum, corn starch, gelatin, etc., (2) disintegrating agents such as corn starch, potato starch, calcium carboxymethylcellulose, etc., (3) lubricating agents such as talc, magnesium stearate, etc. and (4) other pharmaceutically acceptable excipients including pharmaceutically acceptable bulking agents, moisturizing agents, buffers, preservatives, perfumes and the like to obtain tablets, diluted powders, granules or capsules.

In the case of injections, it is possible to prepare solutions or suspensions of one or more compounds of the present invention in pharmaceutically acceptable carriers such as an aqueous or nonaqueous solvent. Examples of solvents which may be used are distilled water for injection, physiological saline solution, Ringer's solution, plant oil, synthetic fatty acid glycerides, higher fatty acid esters, propylene glycol, etc.

It is also possible, depending upon the type of the disease, to prepare pharmaceutical preparations other than the above-mentioned ones which are suitable for therapy depending upon the state of the patient. Exemplary of other pharmaceutical preparations are syrups, suppositories, inhalations, aerosol preparations, collyriums, medicines for external use (e.g. ointments, gels, poultices), etc.

The preferred dosage of the compound of the present invention varies depending upon the subject to be administered (age, body weight, symptoms, etc. of the patient), form of the preparation, method for the administration, term for the administration, etc. To achieve the desired result, the compound may be usually administered by the oral route with a daily dose of 1–1,000 mg per day, preferably 5–600 mg per day, to common adults.

In the case of a parenteral administration such as by injection, the preferred dosage, may be from $\frac{1}{3}$ to $\frac{1}{10}$ of the above-mentioned oral dosages because of the effects of absorption, etc. in the oral route.

Preferred embodiments of the therapeutic agent for intractable vasculitis containing a compound of the present invention represented by the above given formula (1) are:

(1) A therapeutic agent for intractable vasculitis containing a compound represented by the formula (I) wherein one of X and Y represents hydrogen as an active ingredient.

(2) An agent according to the above subparagraph (1) wherein the other of X and Y represents a hydroxyl group.

(3) An agent according to the above subparagraph (2) wherein one of $R_1$ and $R_2$ represents an alkyl group and the other represents hydrogen.

(4) An agent according to the above subparagraph (3) wherein $R_1$ represents an alkyl group.

(5) An agent according to the above subparagraph (4) wherein $R_1$ represents an alkyl group having 1 to 4 carbon atoms.

(6) An agent according to the above subparagraph (5) wherein $R_1$ represents methyl.

(7) A therapeutic agent for intractable vasculitis containing the compound represented by the formula (I) wherein both of X and Y represent hydrogens as an active ingredient.

(8) An agent according to the above subparagraph (7) wherein one of $R_1$ and $R_2$ represents an alkyl group and the other represents hydrogen.

(9) An agent according to the above subparagraph (8) wherein $R_1$ represents an alkyl group.

(10) An agent according to the above subparagraph (9) wherein $R_1$ represents an alkyl group having 1 to 4 carbon atoms.

(11) An agent according to the above subparagraph (10) wherein $R_1$ represents methyl.

(12) An agent according to the above subparagraph (1) wherein the other of X and Y represents an alkoxy group.

(13) An agent according to the above subparagraph (12) wherein R represents an alkyl group and $R_2$ represents hydrogen.

(14) An agent according to the above subparagraph (13) wherein $R_1$ represents methyl.

(15) An agent according to the above subparagraph (1) wherein the other of X and Y represents an alkyl group.

(16) An agent according to the above subparagraph (15) wherein $R_1$ represents an alkyl group and $R_2$ represents hydrogen.

(17) An agent according to the above subparagraph (16) wherein $R_1$ represents methyl.

(18) A therapeutic agent for intractable vasculitis containing the compound represented by the formula (I) wherein X and Y together represent an oxo group as an active ingredient.

(19) An agent according to the above subparagraph (18) wherein $R_1$ represents an alkyl group and $R_2$ represents hydrogen.

(20) An agent according to the above subparagraph (19) wherein R represents methyl.

(21) An agent according to any of the above subparagraphs (1) to (20), which is a therapeutic agent for malignant rheumatoid arthritis.

The most preferred compound for use in the present invention, which has been clinically confirmed as having low toxicity and lower side effects is 5-hydroxy-1-methylhydantoin.

In the following Examples, pharmacological tests were carried out using MRL/lpr mice which are model animals for MRA. MRL/lpr mice have been also known as model animals for systemic lupus erythematosus (SLE) which is a human autoimmune disease. MRL/lpr mice have been known to develop arteritis such as lupus nephritis, arthritis, skin ulcer and auricular infarcted necrosis and lymph node enlargement upon growing older. In addition to the onset of arthritis accompanied by deformation, the existence of RF is noted in MRL/lpr mice. Therefore, MRL/lpr mice are utilized as models for human RA as well. However, since systemic arteritis (cutaneous ulcer and auricular infarcted necrosis) is generated together with chronic arthritis in them, MRL/lpr mice are used as more appropriate models for MRA.

The present invention is illustrated by the following examples wherein all parts, percentages and ratios are by weight, all temperatures are in ° C, and all reactions are conducted at about atmospheric pressure unless indicated to the contrary:

EXAMPLE 1

In this example, the unexpected suppressive action of the hydantoin derivatives of the present invention upon intractable vasculitis is demonstrated by the unexpectedly high survival rate, suppression of arthritis, and suppression of arteritis (cutaneous ulcer or auricular infarcted necrosis) in MRL/lpr mice, which are a pathological animal model for intractable vasculitis.

Experimental Animals

The experimental animals employed were SPF female MRL/lpr mice eight weeks of age, purchased from Nippon Charles River Co., Ltd. Each of 19 mice were placed in each cage in a breeding chamber where the room temperature was 22±2° C., humidity was 55±10% and a brightness/darkness cycle was 12 hours (8:00~20:00). The mice were then quarantined and acclimated for three weeks by giving them feed and tap water freely, and then subjected to the experiments.

Method for Administration of the Test Drugs

The compound of the present invention (100 and 200 mg/kg/day) and MTX as a positive control (2 mg/kg/day) were administered after dissolving in drinking water. The mice of an onset control group were permitted to drink top water freely, the amount of the water taken was measured every day, and concentration of the solution of each drug was adjusted so as to make the dose constant. Amount of the water taken at the initiation of the administration was estimated as 5 ml/mouse based upon the literature and such an amount was given.

Statistical Analysis

The statistical analysis was carried out using Stat View (Long-rank test; Kruskal-Wallis test) and Fisher (direct probability method) which are statistical software programs.

(1) Effect Upon Survival Rate of MRL/lpr Mice

Most of the cause of death of MRL/lpr mice is believed to be renal insufficiency or vascular disturbance and the 50% survival rate was reported to be about 25 weeks old. The number of weeks to the death of MRL/lpr mice in a group administered the compound of the present invention (100 and 200 mg/kg/day), in a group administered MTX (2 mg/kg every two days) as a positive control drug, and in a control group were recorded and the survival rate in each of the groups was investigated. A graph of survival curves of the survival rates was prepared by the Kaplan-Meier method while significant difference was statistically analyzed by the Log-rank test.

Figure 1:
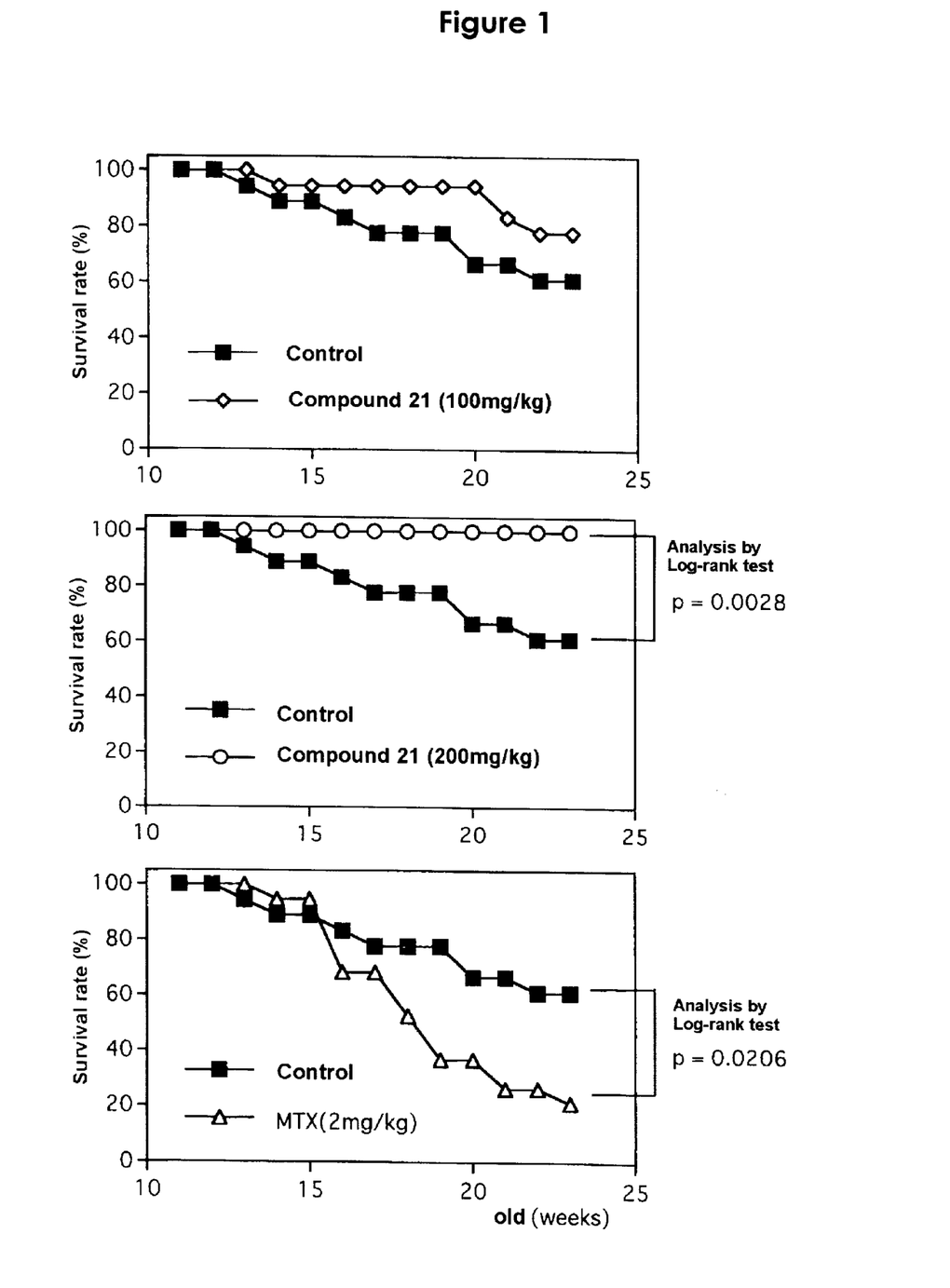
FIG. 1 is an example showing the effect of the hydantoin derivatives of the present invention upon the survival rate of MRL/lpr mice.

An example of the result showing the effect of the compound of the present invention on the survival rate of MRL/lpr mice is shown in FIG. 1. The survival rate (on the 23rd week) of the onset control group was 61% (11 mice/18 mice) while that of a group administered 5-hydroxy-1-methylhydantoin (Compound 21) of the present invention (100 mg/kg/day) was 78% (14 mice/18 mice). Further, in a high-dose group of the Compound 21 of the present invention (200 mg/kg/day), the survival rate was 100% (19 mice/19 mice) where the mortality was none and elongation of the life period was noted significantly ($p<0.01$). However, in the group administered with MTX, the survival rate was significantly ($p<0.05$) lowered to 21% (4 mice/19 mice) showing the strong side effect of the immunosuppressant.

(2) Effect Upon Arthritis

The degree of onset of arthritis in MRL/lpr mice was investigated in the same group constitutions as above. Observations were conducted on the last day (23rd week) of the experiment. The degree of arthritis was evaluated in terms of the value of 0–3 per each leg for the degree of flare and edema, and was expressed by the total score (0–12). With regard to the score for arthritis, "mean value" +"standard error" was calculated for each group, deviation was checked by a Kruskal-Wallis test and, then the significant difference to the control group to which no agent was administered was analyzed by means of a multiple comparison (Dunnet method).

Figure 2:
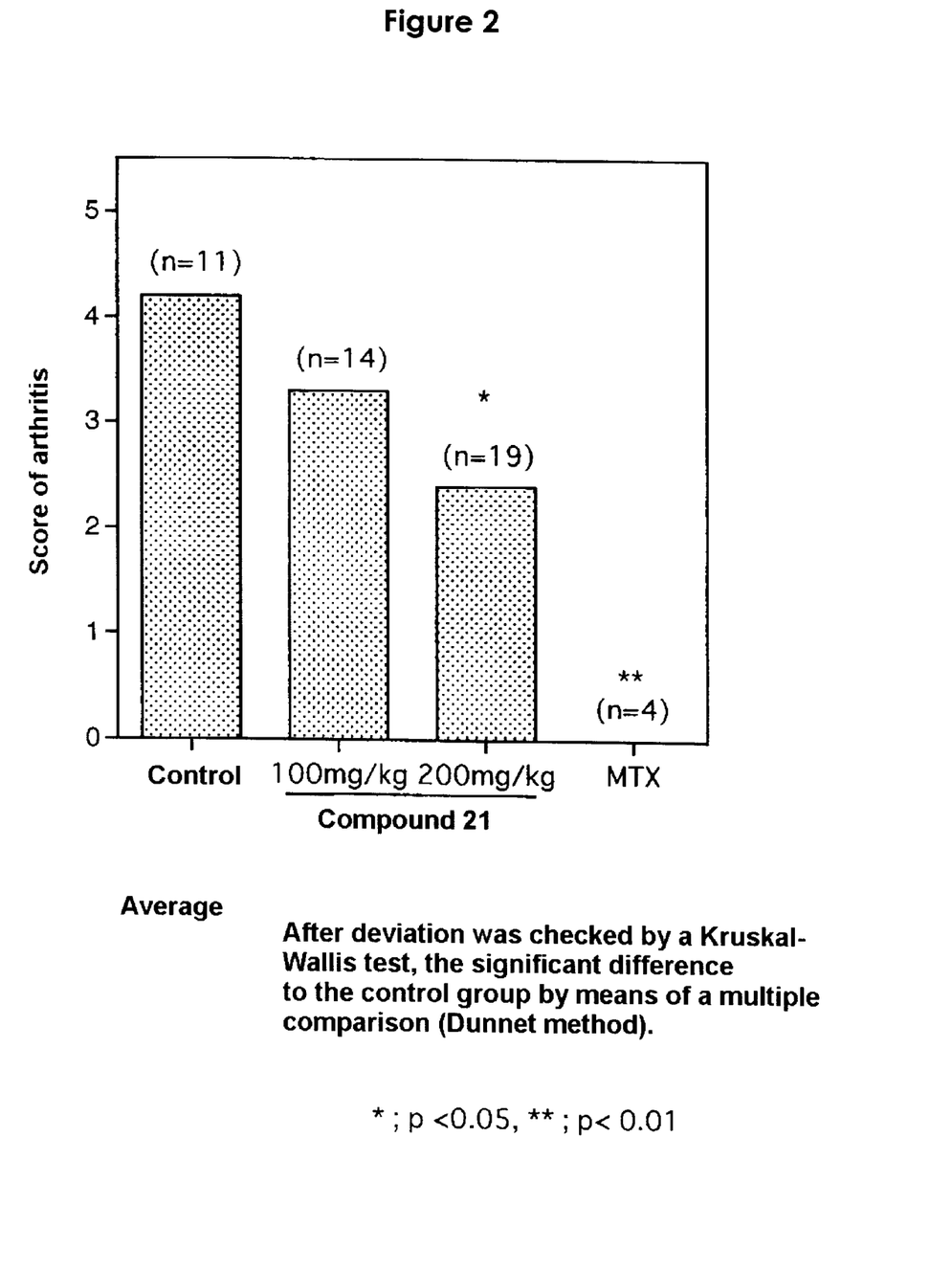
FIG. 2 is an example showing the effect of the hydantoin derivatives of the present invention upon arthritis of MRL/lpr mice.

An example of the results showing the effect of the compound of the present invention upon arthritis of MRL/lpr mice is shown in FIG. 2. The score for arthritis is 4.2 in average in an onset control group. In the low-dose group of Compound 21 of the present invention (100 mg/kg/day), a tendency of suppression was noted and, in the high-dose group of Compound 21 of the present invention (200 mg/kg/day), a significant ($p<0.05$) suppression was noted. Also, a significant ($p<0.01$) suppression was noted in the MTX-administered group as well, but that was a result in the only four cases where the mice were still alive.

(3) Effect Upon Arteritis

Arteritis (ulcerative dermatitis or auricular infarcted necrosis) was investigated in MRL/lpr mice in the same group constitution as above. Evaluation of arteritis was carried out by observing the ulcerative skin of the back and auricular infarcted necrosis on the last day of the experiment (at 23 weeks old) and expressed by its frequency. The judges were not informed of the content of the treatment (such as the fact whether the test drug was administered or not) but were asked to objectively conduct the judgement for the symptom scores (arthritis and arteritis). With regard to the frequency of onset of arteritis, the Fischer direct probability method was used for determining the significant difference to the onset control group.

Figure 3:
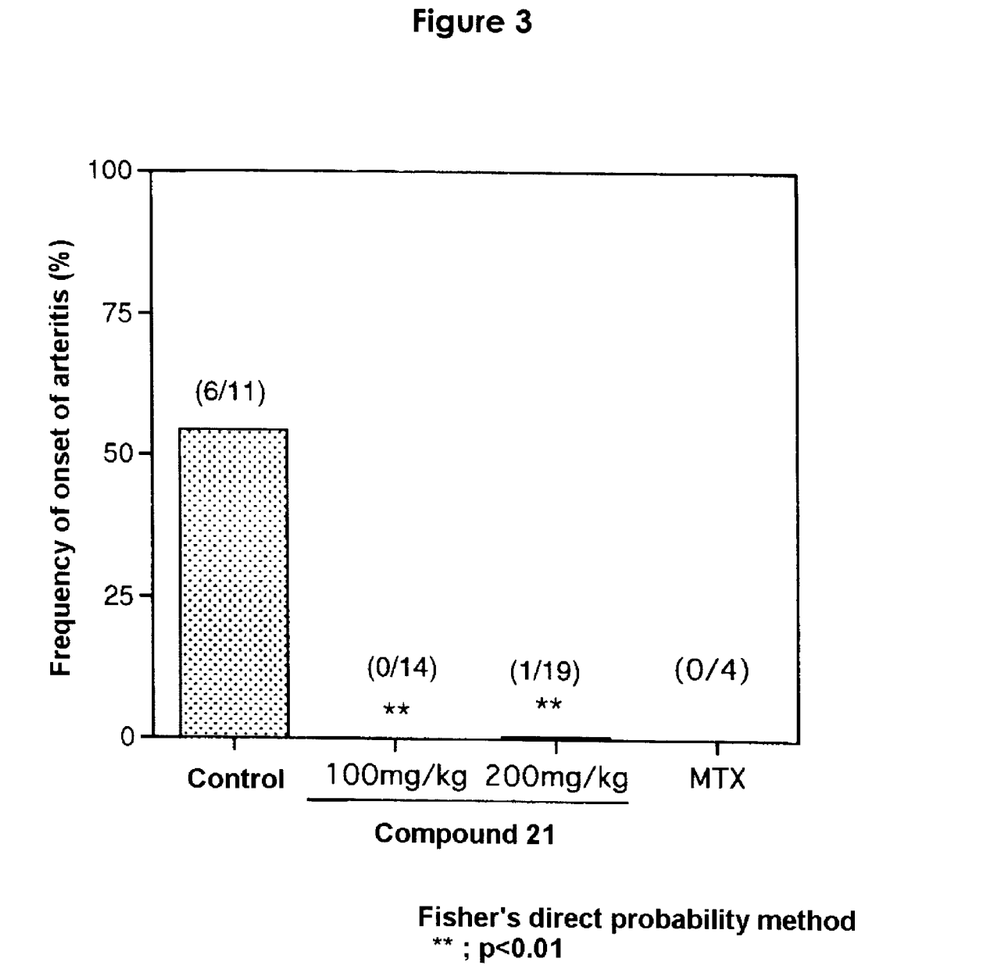
FIG. 3 is an example showing the effect of the hydantoin derivatives of the present invention upon arteritis (cutaneous ulcer or auricular infarcted necrosis) of MRL/lpr mice.

An example of the result of the effect of the compound of the present invention to arteritis (cutaneous ulcer or auricular infarcted necrosis) of MRL/lpr mice is shown in FIG. 3. Cutaneous ulcer or auricular infarcted necrosis was observed from about four to five months of age. The onset frequency of the lesion was 54.5% (6 mice/11 mice) in an onset control group. However, in the MRL/lpr mice administered with the Compound 21 of the present invention, it was 0% (0 mouse/14 mice) and 5.3% (1 mouse/19 mice) in the low-dose group (100 mg/kg/day) and high-dose group (200 mg/kg/day), respectively whereupon remarkable and significant ($p<0.01$) suppression was noted.

EXAMPLE 2

In this example, the unexpected suppressive action of the hydantoin derivatives of the present invention upon intractable vasculitis is demonstrated by the unexpectedly high suppression of the thrombomodulin (TM) level in the plasma of MRL/lpr mice, which are a pathological animal model for intractable vasculitis.

The same MRL/lpr mice (5 weeks old) as employed in Example 1 were purchased and Compound 21 of the present invention was orally administered in the same manner as in Example 1 (10 mice/group, 100 and 200 mg/kg/day). Blood samples were collected at 2 week intervals and thrombomodulin (TM) level in plasma was determined by EIA. TM is a protein on vascular endothelial cells and its level in blood increases by the damage of vascular endothelium such as inflammation. Therefore, TM level in blood can be used as a marker for the onset of vasculitis. C3H/He mice, in which vascular injury does not occur, were used as a control.

Figure 4:
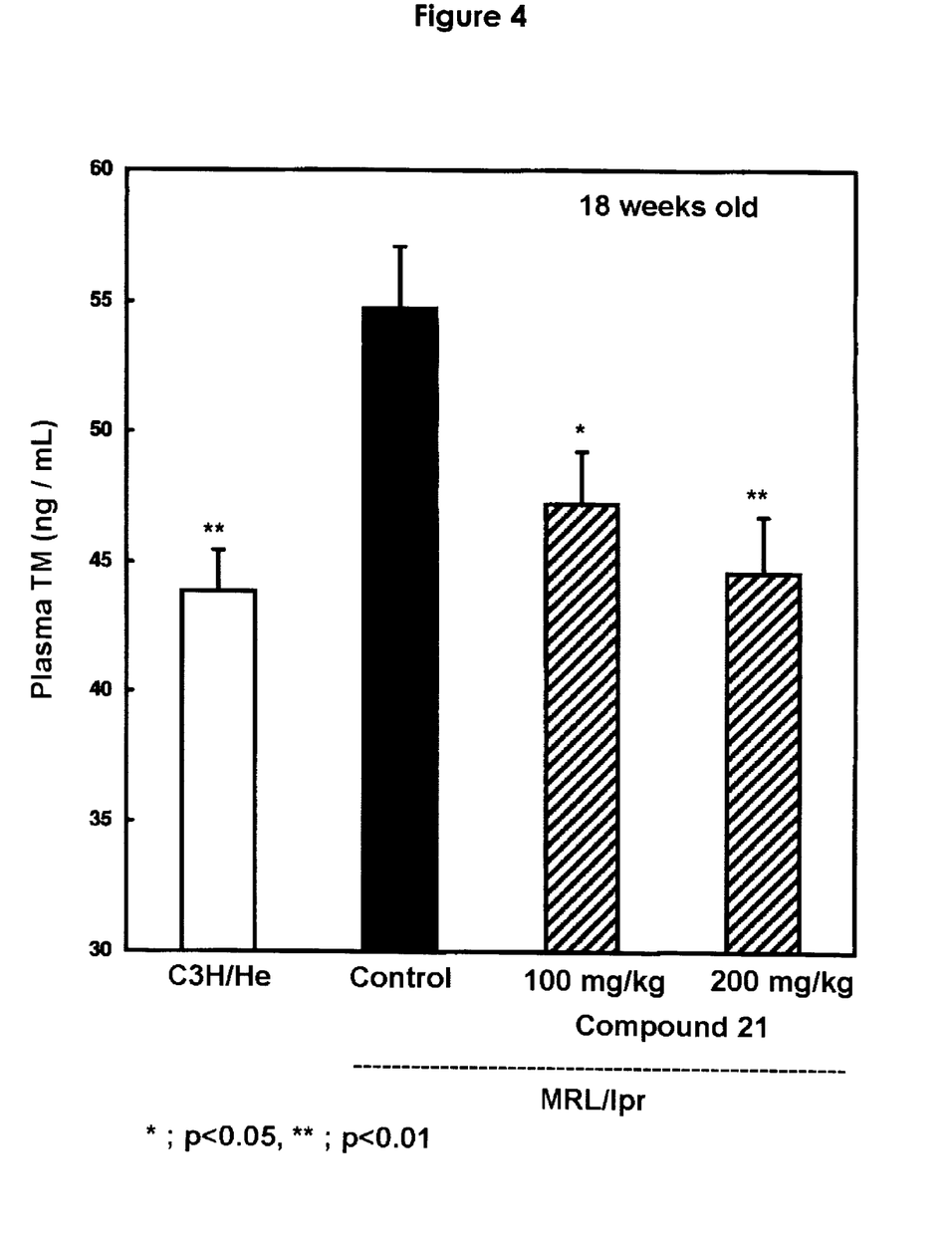
FIG. 4 is an example showing the suppressive effect of the hydantoin derivatives of the present invention against the increase of TM level in blood of MRL/lpr mice.

An example of the results is shown in FIG. 4. TM level in blood of MRL/lpr mice is significantly higher than that of C3H/He mice after 14 weeks of age. On a group of MRL/lpr mice treated with the compound of the present invention, the increase of TM level in blood was prevented and the level was similar to a control level.

It is apparent from the results of FIG. 2 and FIG. 3, that the compounds of the present invention significantly suppressed the generation of arthritis and arteritis (cutaneous ulcer and auricular infarcted necrosis) which were naturally developed in MRL/lpr mice. With aging, this model animal (MRL/lpr mouse) shows characteristic pathological symptoms such as generation of cutaneous ulcer and auricular infarcted necrosis which are able to be judged even from appearance. During the investigation using the said pathological model animals, the present inventors have unexpectedly found that, in the group administered with the compound of the present invention, such auricular necrosis and the like were rarely noted. So, after their intensive investigations, new pharmacological action of the compounds of the present invention was confirmed. Cutaneous ulcer and auricular infarcted necrosis are developed as a result of generation of arteritis and the MRL/lpr mice are recognized to be pathological model animals for intractable vasculitis. Accordingly, the compounds of the present invention are quite useful as therapeutic and preventive agents for intractable vasculitis such as malignant rheumatoid arthritis (MRA), periarteritis nodosa (PN), Wegener's granulomatosis (WG), Kawasaki disease vasculitis, Takayasu's arteritis, Buerger disease, blood vessel Behcet disease, vasculitis of collagen disease, allergic granulomatous vasculitis, nonspecific inflammatory abdominal aortic aneurysm (IAAA), vasculitis related to anti-neutrophil cell antibody (ACNA), anti-phospholipid antibody syndrome and hypersensitive vasculitis.

As shown in FIG. 4, the compound of the present invention significantly prevents an increase of TM level in blood, a marker for the onset of vasculitis. By the data, the inventors can also confirm that the compound of the present invention has an excellent effect on intractable vasculitis.

It is also apparent from FIG. 1 that the compounds of the present invention significantly elongated the survival rate of MRL/lpr mice. Although an immunosuppressive methotrexate (MTX) used as a positive control agent also significantly suppressed the onset of arthritis and arteritis (cutaneous ulcer and auricular infarcted necrosis), it has a strong side effect and the survival rate thereby was lower than that in the group which was not administered a test drug. On the contrary, the compound of the present invention not only suppressed the onset of arthritis and arteritis but also elongated the survival rate. It has been shown already by animal tests and clinical tests that the compounds of the present invention have almost no side effect and, therefore, the compounds of the present invention exhibit both high safety and therapeutic effect as compared with the conventional drug therapies. Consequently, the compounds and compositions of the present invention are drugs which are able to meet the requirements of patients and the clinical field as preferable drugs for intractable vasculitis such as malignant rheumatoid arthritis for which no suitable therapeutic agent is available at present. Accordingly, the present invention has a very high usefulness.

In embodiments of the invention, intractable vasculitis may be treated or prevented in a patient in need of such treatment or prevention by measuring thrombomodulin (TM) level in plasma, determining whether the thrombomodulin (TM) level in the plasma is present at an abnormal level, and administering the hydantoin derivative of the present invention to suppress the TM level to a normal level so as to alleviate symptoms of the disease or condition.

Accordingly, the hydantoin derivatives of the present invention may be employed in accordance with the present invention for the treatment of diseases or conditions other than diabetes, diabetic complications, and those requiring hypoglycemic or hypolipemic action, or lowering of uremic toxin.

What is claimed is:

1. A method for the treatment of intractable vasculitis comprising administering to a patient in need of such treatment a pharmaceutically effective amount of at least one hydantoin derivative represented by the formula (I) or a pharmaceutically acceptable salt, hydrate or complex thereof, said hydantoin derivative being represented by the formula (I):

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

2. A method as claimed in claim 1 wherein said intractable vasculitis is selected from the group consisting of malignant rheumatoid arthritis, periarteritis nodosa, Wegener's granulomatosis, Kawasaki disease vasculitis, Takayasu's arteritis, Buerger disease, blood vessel Behcet disease, vasculitis of collagen disease, allergic granulomatous vasculitis, nonspecific inflammatory abdominal aortic aneurysm, vasculitis related to anti-neutrophil cell antibody, anti-phospholipid antibody syndrome and hypersensitive vasculitis.

3. A method as claimed in claim 1 wherein said intractable vasculitis is malignant rheumatoid arthritis.

4. A method as claimed in claim 1 wherein one of X and Y is hydrogen.

5. A method as claimed in claim 4 wherein the other of X and Y is a hydroxyl group.

6. A method as claimed in claim 5 wherein one of $R_1$ and $R_2$ is an alkyl group and the other is hydrogen.

7. A method as claimed in claim 6 wherein $R_1$ is methyl.

8. A method as claimed in claim 3 wherein one of X and Y is a hydroxyl group.

9. A method as claimed in claim 8 wherein the other of X and Y is hydrogen.

10. A method as claimed in claim 9 wherein one of $R_1$ and $R_2$ is an alkyl group and the other is hydrogen.

11. A method as claimed in claim 10 wherein $R_1$ is methyl.

12. A method for treating intractable vasculitis comprising administering to a patient in need of such treatment a pharmaceutical composition comprising a pharmaceutically effective amount of at least one hydantoin derivative represented by the formula (I) or a pharmaceutically acceptable salt, hydrate or complex thereof, and a pharmaceutically acceptable carrier, said hydantoin derivative being represented by the formula (I):

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

13. A method as claimed in claim 12 wherein said intractable vasculitis is selected from the group consisting of malignant rheumatoid arthritis, periarteritis nodosa, Wegener's granulomatosis, Kawasaki disease vasculitis, Takayasu's arteritis, Buerger disease, blood vessel Behcet disease, vasculitis of collagen disease, allergic granulomatous vasculitis, nonspecific inflammatory abdominal aortic aneurysm, vasculitis related to anti-neutrophil cell antibody, anti-phospholipid antibody syndrome and hypersensitive vasculitis.

14. A method as claimed in claim 12 wherein said intractable vasculitis is malignant rheumatoid arthritis.

15. A method as claimed in claim 12 wherein one of X and Y is hydrogen.

16. A method as claimed in claim 15 wherein the other of X and Y is a hydroxyl group.

17. A method as claimed in claim 16 wherein one of $R_1$ and $R_2$ is an alkyl group and the other is hydrogen.

18. A method as claimed in claim 17 wherein $R_1$ is methyl.

19. A method for the treatment of intractable vasculitis comprising determining the presence of thrombomodulin (TM) in plasma symptomatic of said disease, and administering to a patient in need of such treatment a pharmaceutically effective amount of at least one hydantoin derivative represented by the formula (I) or a pharmaceutically acceptable salt, hydrate or complex thereof to substantially suppress the level of thrombomodulin in plasma symptomatic of said disease, said hydantoin derivative being represented by the formula (I):

(I)

wherein, each of $R_1$ and $R_2$, which may be the same or different, is hydrogen, an alkyl group or a cycloalkyl group; and each of X and Y, which may be the same or different, is hydrogen, a hydroxyl group, an alkyl group or an alkoxy group, or X and Y together is an oxo group.

20. A method as claimed in claim 19 wherein said intractable vasculitis is selected from the group consisting of malignant rheumatoid arthritis, periarteritis nodosa, Wegener's granulomatosis, Kawasaki disease vasculitis, Takayasu's arteritis, Buerger disease, blood vessel Behcet disease, vasculitis of collagen disease, allergic granulomatous vasculitis, nonspecific inflammatory abdominal aortic aneurysm, vasculitis related to anti-neutrophil cell antibody, anti-phospholipid antibody syndrome and hypersensitive vasculitis.

\* \* \* \* \*